United States Patent [19]

Hinney et al.

[11] Patent Number: 5,248,833

[45] Date of Patent: Sep. 28, 1993

[54] PROCESS FOR PURIFYING POLYOLS MADE WITH DOUBLE METAL CYANIDE CATALYSTS

[75] Inventors: Harry R. Hinney, Cross Lanes; Don S. Wardius, Charleston, both of W. Va.

[73] Assignee: Arco Chemical Technology, L.P., Wilmington, Del.

[21] Appl. No.: 948,275

[22] Filed: Sep. 22, 1992

[51] Int. Cl.$^5$ ............................................. C07C 41/36
[52] U.S. Cl. .................................. 568/621; 560/181; 560/191
[58] Field of Search ......................... 568/621; 560/181

[56] References Cited

U.S. PATENT DOCUMENTS

| | | | |
|---|---|---|---|
| 3,278,457 | 10/1966 | Milgrom | 260/2 |
| 3,278,458 | 10/1966 | Belner | 260/2 |
| 3,427,256 | 2/1969 | Milgrom | 252/431 |
| 3,427,334 | 2/1969 | Belner | 260/429 |
| 3,829,505 | 8/1974 | Herold | 260/611 |
| 4,355,188 | 10/1982 | Herold et al. | 568/620 |
| 4,472,560 | 9/1984 | Kuyper et al. | 526/120 |
| 4,477,589 | 10/1984 | van der Hulst et al. | 502/169 |
| 4,721,818 | 1/1988 | Harper et al. | 568/120 |
| 4,877,906 | 10/1989 | Harper | 568/621 |
| 4,987,271 | 1/1991 | Watabe et al. | 568/621 |
| 5,010,047 | 4/1991 | Schuchardt | 502/24 |
| 5,099,075 | 3/1992 | Katz et al. | 568/621 |
| 5,144,093 | 9/1992 | Reisch et al. | 568/621 |
| 5,158,922 | 10/1992 | Hinney et al. | 502/175 |

FOREIGN PATENT DOCUMENTS 0406440 9/1991 European Pat. Off. .

OTHER PUBLICATIONS

"Preparation of High Molecular Weight Polyols Using Double Metal Cyanide Catalysts" J. L. Schuchardt and S. D. Harper, *Proceedings of the SPI—32nd Annual Polyurethane Technical Marketing Conference, (Oct. 1989) pp. 360-364.*

"Hexacyanometalate Salt Complexes as Catalysts for Epoxide Polymerization," *Advances in Chemistry Series: Polymerization Kinetics and Technology,* No. 128 (1973) pp. 208-229. R. J. Herold and R. A. Livigni.

*Primary Examiner*—Howard T. Mars
*Attorney, Agent, or Firm*—Jonathan L. Schuchardt

[57] ABSTRACT

A process for purifying polyether polyols prepared using double metal cyanide (DMC) catalysts is disclosed. The process involves combining a mixture of the polyol and a $C_1$-$C_6$ aliphatic alcohol with an amount of a chelating agent effective to form an insoluble complex with the catalyst, then filtering the polyol mixture to remove the insoluble complex. The process, which requires that the polyol and alcohol be present in a relative weight ratio of from 1:1 to 100:1, is effective for removing DMC residues and any cations introduced with the chelating agent.

19 Claims, No Drawings

PROCESS FOR PURIFYING POLYOLS MADE WITH DOUBLE METAL CYANIDE CATALYSTS

FIELD OF THE INVENTION

The invention relates to polyol purification, and more particularly, to a method for removing double metal cyanide catalyst residues from a polyether polyol with the aid of a chelating agent.

BACKGROUND OF THE INVENTION

Polyether polyols prepared using double metal cyanide (DMC) catalysts such as zinc hexacyanocobaltate are well known. (See, for example, U.S. Pat. Nos. 3,278,457 and 4,477,589; R. J. Herold and R. A. Livigni, *Adv. in Chem. Series: Polymerization Kinetics and Technology*, No. 128 (1973) 208; J. L. Schuchardt and S. D. Harper, *Proceedings of the SPI—32nd Annual Polyurethane Technical/Marketing Conference*, Oct. 1989, p. 360). A key advantage of these polyols compared with those prepared with a conventional (KOH) catalyst is the high functionality—even at high equivalent weight—and low unsaturation of polyols made with DMC catalysts.

Removal of double metal cyanide catalyst residues from polyether polyols promotes long-term storage stability and consistent polyol performance in urethane formulation. Polyols that contain catalyst residues generate volatile impurities that give the polyol an undesirable odor. In addition, the catalyst residues often catalyze undesired reactions during polyurethane formulation.

Unfortunately, DMC catalyst residues are often troublesome to remove from polyether polyols. Typical catalyst removal methods for conventional base catalysts—such as heating the polyol with magnesium silicate, passing the polyol through an ion-exchange resin, or acid-treating the polyol followed by ion-exchange treatment—are generally ineffective for removing DMC catalyst residues. More rigorous methods include heating the catalyst-containing polyol with alkali metals, alkali metal hydroxides, or alkali metal hydrides (see U.S. Pat. Nos. 4,355,188 and 4,721,818). Unfortunately, these methods are often slow, use expensive, toxic, and/or highly reactive reagents, introduce unwanted color into the polyol, and give inconsistent catalyst removal performance. In another process (U.S. Pat. No. 5,010,047), DMC catalyst residues are removed by diluting the polyol with a nonpolar solvent such as hexanes or toluene, followed by filtration. This process uses a large amount of solvent and filter aid.

Watabe et al. (U.S. Pat. No. 4,987,271) teach a method for purifying polyether polyols prepared using DMC catalysts. The method comprises heating the catalyst-containing polyol with a pH buffer solution, then (optionally) adding a chelating agent to the mixture, adding an adsorbent (magnesium silicate, alumina, etc.) or ion-exchange resin, and filtering the mixture. When a chelating agent is used, ammonia can be used instead of a pH buffer.

Another known process for removing DMC catalyst residues from polyether polyols involves (a) heating a polyol that contains DMC catalyst residues with 88:12 (w/w) isopropanol/water (1 *part of polyol to* 2 *parts of isopropanol/water*) at 80° C. for 8 h in the presence of 0.5 weight percent of dipotassium EDTA; (b) filtering the resulting EDTA complex from the polyol; (c) passing the polyol solution through a mixed anion/cation ion-exchange resin bed; and (d) stripping the isopropanol/water away from the polyol. This process is rather impractical commercially because of the large volume of solvent that must be stored, transferred, and stripped, and the need for ion-exchange facilities. The method suffers from one additional important drawback: potassium ions introduced into the polyol with the dipotassium EDTA are difficult to remove when 2 parts of isopropanol/water are used for each part of polyol unless the ion-exchange treatment is included.

Still needed in the art is a reliable, practical process for removing DMC catalysts from polyether polyols. A preferred process would avoid pre-treatment of the polyol with toxic, reactive reagents, and would eliminate the need for adsorbents, which add to raw material and waste disposal costs. A preferred process would use a minimum amount of solvent, and would allow removal of double metal cyanide catalyst residues without introducing additional cationic moieties. A preferred process would eliminate the need for ion-exchange treatments.

SUMMARY OF THE INVENTION

Objects of the invention: (1) a commercially practical and economical process for purifying double metal cyanide catalyst-containing polyether polyols; (2) a process that overcomes the need for prolonged chemical pre-treatment of the polyol; (3) a process that avoids toxic, expensive, and highly reactive reagents; (4) a process that gives reliable, reproducible, effective removal of DMC catalyst residues; (5) a process that minimizes the raw material and waste disposal costs of an adsorbent; (6) a process that permits removal of DMC catalyst residues while also allowing removal of an cationic moieties introduced into the polyol when a chelating agent is used; (7) a process that overcomes the need for ion-exchange treatment.

The invention is a process for purifying a polyether polyol prepared using a double metal cyanide (DMC) catalyst. The process comprises (a) combining a polyether polyol that contains DMC catalyst residues with a $C_1$–$C_6$ aliphatic alcohol and an amount of a chelating agent effective to form an insoluble complex with the catalyst residues; and (b) filtering the resulting mixture to remove the insoluble complex from the polyol. Importantly, the relative weight ratio of the polyether polyol to the $C_1$–$C_6$ aliphatic alcohol is within the range of about 1:1 to about 100:1. We have surprisingly found that this particular range of polyol/alcohol proportions consistently permits removal of DMC residues and, at the same time, allows complete removal of any cations (sodium, potassium, calcium, ammonium, etc.) introduced with the chelating agent.

DETAILED DESCRIPTION OF THE INVENTION

The polyether polyols purified by the process of the invention are those produced by polymerizing one or more epoxides in the presence of a hydroxyl group-containing initiator and a double metal cyanide catalyst. The polyols optionally include recurring units of other monomers (such as anhydrides) that will copolymerize with epoxides in the presence of a DMC catalyst. For example, a polyetherester copolymer prepared by copolymerizing maleic anhydride and propylene oxide in the presence of a DMC catalyst is suitable for use in the invention. Preferably, the polyether polyols are polyoxyalkylene polyethers derived from propylene oxide and/or ethylene oxide, and have nominal functionalities from 1 to 8. Preferably, the polyether polyols have a number average molecular weight within the range of about 250 to about 25,000. More preferred are polyether polyols having number average molecular weights within the range of about 1,000 to about 20,000.

The double metal cyanide (DMC) catalysts used to prepare the polyether polyols are well known in the art. The preparation of these catalysts and their use to prepare polyether polyols from epoxides is fully described in references such as U.S. Pat. Nos. 3,427,256, 3,427,334, 3,278,457, 3,278,458, 4,477,589, 4,472,560, and 4,987,271. The teachings of these patents are incorporated herein by reference in their entirety.

Zinc hexacyanocobaltate complexes are commonly used for polyether polyol synthesis. These catalysts are easily prepared and highly active. Complete removal of the residual catalyst from the polyether polyol product following epoxide polymerization, however, is particularly troublesome.

In the process of the invention, a polyether polyol that contains double metal cyanide residues is combined with a $C_1$–$C_6$ aliphatic alcohol and an amount of a chelating agent effective to form an insoluble complex with the catalyst residues.

The $C_1$–$C_6$ aliphatic alcohol is a linear, branched, or cyclic alcohol. Examples of suitable alcohols include, but are not limited to, methanol, ethanol, 1-propanol, isopropanol, 1-hexanol, cyclohexanol, isopentanol, and the like, and mixtures thereof. Preferred alcohols are $C_1$–$C_4$ aliphatic alcohols. Particularly preferred is isopropanol.

The $C_1$–$C_6$ aliphatic alcohol can be used alone, but is preferably used in combination with water. When an aqueous alcohol mixture is used, it is preferred that the aliphatic alcohol be present in the mixture in an amount within the range of about 50 to about 95 weight percent. More preferred is the range from about 70 to about 90 weight percent alcohol. Aqueous mixtures of water-miscible ($C_1$–$C_4$) alcohols are preferred. For example, a constant-boiling mixture of isopropanol and water, which is about 88:12 (w/w) isopropanol/water, is suitable for use in the process. If the alcohol is omitted completely, and only water is used with the chelating agent, removal of the DMC catalyst residues is typically less than satisfactory.

The relative amounts of polyether polyol and $C_1$–$C_6$ aliphatic alcohol (or alcohol/water mixture) used are important. According to the invention, the relative weight ratio of the polyether polyol to the $C_1$–$C_6$ aliphatic alcohol is within the range of about 1:1 to about 100:1. A more preferred range is from about 2:1 to about 50:1. Most preferred is the range from about 4:1 to about 20:1. If the ratio of polyether polyol to $C_1$–$C_6$ aliphatic alcohol exceeds about 100:1, removal of the DMC catalyst residues is typically incomplete. On the other hand, if this ratio is less than about 1:1, then cationic moieties introduced with the chelating agent are difficult to remove from the polyol/alcohol mixture.

A chelating agent is used in the process of the invention. Any known chelating agent can be used. Chelating agents are compounds that can form a complex with a metal ion in which the compound binds the metal with two coordinate links. Preferred chelating agents are ethylenediaminetetraacetic acid (EDTA) and its salts, particularly the ammonium, lithium, sodium, potassium, calcium, magnesium, and iron salts, and hydrates thereof. Particularly preferred is EDTA (free acid) because its use introduces no additional cationic moieties.

Any desired amount of chelating agent can be used. The amount needed will typically depend on the amount of DMC catalyst present in the polyol, and is the amount effective to form an insoluble complex with the DMC catalyst residues. It is preferred to use an amount of chelating agent within the range of about 0.001 to about 5 weight percent based on the amount of polyether polyol treated. A more preferred range is from about 0.01 to about 2 wt. %. Most preferred is the range from about 0.1 to about 1 wt. %. The chelating agent can be introduced into the polyol by any desired method. Solid chelating agents can be added as is; often it will be more convenient to introduce the chelating agent as an aqueous solution.

The polyether polyol, chelating agent, and $C_1$–$C_6$ aliphatic alcohol can be combined and maintained at any desired temperature. A practical upper limit is typically the boiling point of the $C_1$–$C_6$ aliphatic alcohol. Preferably, the polyol, alcohol, and chelating agent are combined and mixed at a temperature within the range of about 20° C. to about 160° C. A more preferred range is from about 20° C to about 80° C.

We believe that the chelating agent forms a complex with the double metal cyanide catalyst residues that is insoluble in the polyol/alcohol mixture. The best evidence of this is that the DMC catalyst residues can be removed effectively by filtration following combination of the polyether polyol, $C_1$–$C_6$ aliphatic alcohol, and chelating agent.

The filtration can be performed by any conventional method, and can be carried out at, above, or below atmospheric pressure. If desired, an adsorbent such as magnesium silicate, diatomaceous earth, alumina, or the like can be used to improve catalyst removal. An advantage of the invention is that such adsorbents are normally not needed, so the raw material costs of the process are reduced. In addition, the process of the invention avoids costly disposal of an adsorbent filter cake, which, in addition to the adsorbent, normally contains a substantial amount (typically about 2 weight percent based on the amount of treated polyol) of valuable, yet wasted polyether polyol.

Unlike previous methods that involve prolonged pre-treatment of the polyether polyol at elevated temperature with harsh reagents such as alkali metals, alkali metal hydroxides, and alkali metal hydrides, the process of the invention requires no pre-treatment step. A beneficial result is that the polyols purified by the process of the invention remain low in color. In contrast, pre-treatment methods commonly used in the art often induce unwanted color development in the polyol.

The chelating agents used in the process of the invention have generally low reactivity and low toxicity. This is an advantage because their use presents no special handling concerns such as, for example, the need for slow, careful reagent addition, or the need for a moisture-free, inert atmosphere.

Another advantage of the invention is that the process permits essentially complete removal of cationic moieties introduced during the treatment. The use of alkali metal compounds or an ammonia-based buffer solution in a pre-treatment step always presents the problem of how to ultimately remove the alkali metal or ammonium compounds (in addition to the DMC catalyst residues) from the polyol. Results are often unpredictable. Alkali metal ions and other cations are also commonly introduced into the polyol when a chelating agent is added according to the process of the invention. However, we have surprisingly found that these cationic moieties are predictably and effectively removed—along with the DMC catalyst residues—when the polyether polyol/$C_1$-$C_6$ aliphatic alcohol weight ratio is kept within the range of about 1:1 to about 100:1.

If desired, an ion-exchange resin can optionally be used to assist in removal of cationic moieties from the polyol, although the process of the invention overcomes the need to use such a resin (as shown, for example, in U.S. Pat. No. 4,987,271).

Filtration can usually follow shortly after combination of the polyol, alcohol, and chelating agent. Satisfactory formation of the insoluble complex is typically complete within about 2 hours. Longer treatment times can be used if desired.

The following examples merely illustrate the invention. Those skilled in the art will recognize numerous variations that are within the spirit of the invention and scope of the claims.

EXAMPLES 1-15

The polyether polyols are prepared by polymerizing propylene oxide in the presence of a hydroxyl group-containing initiator and zinc hexacyanocobaltate. The catalyst is prepared according to the method of U.S. Pat. No. 5,158,922. The polymerizations are performed as in U.S. Pat. No. 3,829,505 to make a 4000 molecular weight polyoxypropylene diol (from a 425 mol. wt. polyoxypropylene diol initiator) and a 6000 molecular weight polyoxypropylene triol (from a 700 mol. wt. polyoxypropylene triol initiator).

A polyether polyol sample containing about 250-500 ppm of residual zinc hexacyanocobaltate catalyst (250 g polyol) is dissolved in the desired amount (see Tables 1-4) of constant-boiling aqueous isopropanol (88:12 (w/w) isopropanol/water), and the solution is optionally heated to the desired treatment temperature. The chelating agent (1.25 g, 0.50 wt. % based on the amount of polyol, see Tables 1-4) is added, and the mixture is continuously stirred. Samples are removed by syringe at timed intervals. The samples are filtered through 1.2 um filter paper, and are stripped to remove volatile materials. The concentrated samples are analyzed by ICP emission spectroscopy to determine the remaining amounts of zinc and cobalt, and by atomic absorption spectroscopy to determine the content of other metals.

This procedure is modified slightly for Comparative Examples 10 and 14. In these examples, the polyol is combined with 3 wt. % water, and no isopropanol. Also, the samples are stripped to remove water before filtration and analysis.

Catalyst removal results for all of the examples appear in Tables 1-4.

As shown in Table 1, removal of both DMC catalyst residues and potassium from a 6000 molecular weight polyoxypropylene triol is reasonably complete within about 2 hours at either 78° C. (Example 2) or 22° C. (Example 3).

Comparative Example 4 (Table 2) shows the problem of high residual potassium when a 1:2 polyol/alcohol mixture is used. In this case, the polyol is a 4000 molecular weight polyoxypropylene diol. Examples 5-7 show that polyol/alcohol ratios of 2:1, 4:1, and 10:1 give essentially complete removal of both DMC catalyst residues and potassium introduced with the chelating agent. At the other extreme is Comparative Example 9, which shows the need to include some $C_1$-$C_6$ aliphatic alcohol in the process: if the alcohol is omitted, residual DMC catalyst levels following treatment are too high. Example 8 shows that the aliphatic alcohol can be used without adding any water to it. Comparative Example 10 shows the effect of omitting the alcohol, and using only water with the chelating agent. Although DMC catalyst levels are reduced, they are still higher than desirable.

Results with calcium disodium EDTA as the chelating agent appear in Table 3. The problem of high residual sodium is alleviated by the use of a 2:1 polyol/alcohol solution (Example 12) compared with a 1:2 mixture (Comparative Example 11). As shown in Table 4, EDTA (the free acid) can also be advantageously used in the process of the invention, thus avoiding introduction of additional cationic moieties. Note again that water alone is generally unsatisfactory (Comparative Example 14); some alcohol is necessary for best results.

The preceding examples are meant only as illustrations; the true metes and bounds of the invention are defined only by the following claims.

TABLE 1

Catalyst Removal from 6000 MW Triol using Dipotassium EDTA[1]

| Ex # | Polyol[2]/IPA[3] | Temp. °C. | Time[5], h | Residual Metals[4,6], ppm | | |
|---|---|---|---|---|---|---|
| | | | | Co | Zn | K |
| C1 | 1:2 | 78 | 1 | 1.5 | 3.2 | <60 |
| | | | 2 | 1.3 | 6.2 | <60 |
| 2 | 2:1 | 78 | 1 | 22 | 41 | 14 |
| | | | 2 | 3.8 | 6 | 3.9 |
| 3 | 2:1 | 22 | 1 | 7.7 | 17 | 1.5 |
| | | | 2 | 6.2 | 13 | 1.5 |

[1]All samples treated with 0.5 wt. % EDTA derivative
[2]Polyol = 6000 molecular weight polyoxypropylene triol
[3]IPA = constant boiling mixture of isopropanol/water (88:12)
[4]Untreated polyol has Co = 30 ppm. Zn = 71 ppm.
[5]Workup: Sample withdrawn at time indicated is filtered through a 1.2 um filter, stripped, and analyzed.
[6]Analysis for Zn, Co: ICP emission spectroscopy; analysis for K: atomic absorption spectroscopy.

TABLE 2

Catalyst Removal from 4000 MW Diol using Dipotassium EDTA[1]

| Ex # | Polyol[2]/IPA[3] | Temp. °C. | Time[5], h | Residual Metals[4,6], ppm | | |
|---|---|---|---|---|---|---|
| | | | | Co | Zn | K |
| C4 | 1:2 | 78 | 1 | <1 | 1.4 | 20 |
| | | | 2 | 2.1 | 2.4 | 32 |
| 5 | 2:1 | 78 | 1 | 1.7 | 2.8 | 8.2 |
| | | | 2 | <1 | <1 | 12 |
| 6 | 4:1 | 78 | 1 | 1.4 | 2.8 | 2.4 |
| | | | 2 | 1.9 | 2.5 | 2.9 |
| 7 | 10:1 | 78 | 1 | <1 | 1.3 | 1.2 |
| | | | 2 | <1 | 1.1 | <1 |
| 8 | 4:1 | 78 | 1 | 12 | 22 | 2.0 |
| | | | 2 | 4.4 | 6.2 | 2.8 |
| C9 | 100% Polyol | 78 | 1 | 12.6 | 27.2 | <1 |
| | | | 2 | 12.2 | 26.1 | <1 |
| C10 | 3 wt. % $H_2O$ | 78 | 1 | 18 | 34 | 3.1 |
| | | | 2 | 16 | 31 | 4.2 |

[1]All samples treated with 0.5 wt. % EDTA derivative
[2]Polyol = 4000 molecular weight polyoxypropylene diol
[3]IPA = constant boiling mixture of isopropanol/water (88:12) except Example 8, which uses 100% isopropanol.
[4]Untreated polyol has Co = 47 ppm. Zn = 110 ppm.
[5]Workup: Sample withdrawn at time indicated is filtered through a 1.2 um filter, stripped, and analyzed.
[6]Analysis for Zn, Co: ICP emission spectroscopy; analysis for K: atomic absorption spectroscopy.

TABLE 3

Catalyst Removal from 4000 MW Diol using Calcium Disodium EDTA[1]

| Ex # | Polyol[2]/IPA[3] | Temp. °C. | Time[5], h | Residual Metals[4,6], ppm | | | |
|---|---|---|---|---|---|---|---|
| | | | | Co | Zn | Na | Ca |
| C11 | 1:2 | 78 | 1 | 1.1 | 7.0 | 40 | 1.2 |
| | | | 2 | 1.4 | 4.4 | 34 | <1 |
| 12 | 2:1 | 78 | 1 | <1 | <1 | 9.7 | <1 |
| | | | 2 | <1 | <1 | 13 | <1 |

[1] All samples treated with 0.5 wt. % EDTA derivative
[2] Polyol = 4000 molecular weight polyoxypropylene diol
[3] IPA = constant boiling mixture of isopropanol/water (88:12)
[4] Untreated polyol has Co = 47 ppm, Zn = 110 ppm.
[5] Workup: Sample withdrawn at time indicated is filtered through a 1.2 um filter, stripped, and analyzed.
[6] Analysis for Zn, Co: ICP emission spectroscopy; analysis for K: atomic absorption spectroscopy.

TABLE 4

Catalyst Removal from 4000 MW Diol using EDTA(Free Acid)[1]

| Ex # | Polyol[2]/IPA[3] | Temp. °C. | Time[5], h | Residual Metals[4,6], ppm | |
|---|---|---|---|---|---|
| | | | | Co | Zn |
| C13 | 1:2 | 78 | 1 | 1.6 | 3.6 |
| | | | 2 | 2.1 | 4.9 |
| C14 | 3 wt. % H$_2$O | 78 | 1 | 16 | 40 |
| | | | 2 | 20 | 44 |
| 15 | 2:1 | 78 | 1 | <1 | 1.0 |
| | | | 2 | <1 | 1.1 |

[1] All samples treated with 0.5 wt. % EDTA derivative
[2] Polyol = 4000 molecular weight polyoxypropylene diol
[3] IPA = constant boiling mixture of isopropanol/water (88:12)
[4] Untreated polyol has Co = 47 ppm, Zn = 110 ppm.
[5] Workup: Sample withdrawn at time indicated is filtered through a 1.2 um filter, stripped, and analyzed.
[6] Analysis for Zn, Co: ICP emission spectroscopy.

We claim:

1. A process for purifying a polyether polyol prepared using a double metal cyanide catalyst, said process comprising:

(a) combining a polyether polyol that contains double metal cyanide catalyst residues with a $C_1$–$C_6$ aliphatic alcohol and a chelating agent selected from the group consisting of ethylenediaminetetraacetic acid (EDTA) and EDTA salts containing one or more cations selected from the group consisting of lithium, sodium, potassium, magnesium, calcium, ammonium, and iron, in an amount effective to form an insoluble complex with the catalyst residues; and (b) filtering the resulting mixture to remove the insoluble complex from the polyol;

wherein the relative weight ratio of the polyether polyol to the $C_1$–$C_6$ aliphatic alcohol is within the range of about 1:1 to about 100:1.

2. The process of claim 1 wherein the polyether polyol has a nominal functionality of from 1 to 8.

3. The process of claim 1 wherein the polyether polyol is a copolymer of ethylene oxide and propylene oxide.

4. The process of claim 1 wherein the polyether polyol has a number average molecular weight within the range of about 250 to about 25,000.

5. The process of claim 1 wherein the catalyst residues are derived from a zinc hexacyanocobaltate catalyst.

6. The process of claim 1 wherein the $C_1$–$C_6$ aliphatic alcohol is selected from the group consisting of methanol, ethanol, n-propanol, and isopropyl alcohol.

7. The process of claim 1 wherein an aqueous mixture containing from about 50 to about 95 weight percent of a $C_1$–$C_4$ aliphatic alcohol is combined with the polyether polyol and the chelating agent.

8. The process of claim 1 wherein the chelating agent is EDTA.

9. The process of claim 1 wherein the combined polyol, alcohol, and chelating agent are combined at a temperature within the range of about 20° C. to about 80° C.

10. The process of claim 1 wherein the relative weight ratio of the polyether polyol to the $C_1$–$C_6$ aliphatic alcohol is within the range of about 2:1 to about 10:1.

11. A process for purifying a polyether polyol prepared using a double metal cyanide catalyst, said process comprising:

(a) combining a polyether polyol that contains double metal cyanide catalyst residues with an aqueous $C_1$–$C_6$ aliphatic alcohol mixture and an amount of a chelating agent effective to form an insoluble complex with the catalyst residues; and (b) filtering the resulting mixture to remove the insoluble complex from the polyol;

wherein the relative weight ratio of the polyether polyol to the aqueous $C_1$–$C_6$ aliphatic alcohol mixture is within the range of about 2:1 to about 10:1, and the aqueous $C_1$–$C_6$ aliphatic alcohol mixture contains from about 50 to about 95 weight percent of the aliphatic alcohol; and wherein the chelating agent is selected from the group consisting of ethylenediaminetetraacetic acid (EDTA) and EDTA salts containing one or more cations selected from the group consisting of lithium, sodium, potassium, magnesium, calcium, ammonium, and iron.

12. The process of claim 11 wherein the polyether polyol has a nominal functionality of from 1 to 8.

13. The process of claim 11 wherein the polyether polyol has a number average molecular weight within the range of about 250 to about 25,000.

14. The process of claim 11 wherein the catalyst residues are derived from a zinc hexacyanocobaltate catalyst.

15. The process of claim 11 wherein the $C_1$–$C_6$ aliphatic alcohol is selected from the group consisting of methanol, ethanol, n-propanol, and isopropyl alcohol.

16. The process of claim 11 wherein the aqueous aliphatic alcohol mixture contains a $C_1$–$C_4$ aliphatic alcohol.

17. The process of claim 11 wherein the chelating agent is EDTA.

18. The process of claim 11 wherein the combined polyol, aqueous alcohol mixture, and chelating agent are reacted at a temperature within the range of about 20° C. to about 80° C.

19. A process for purifying a polyether polyol prepared using a zinc hexacyanocobaltate catalyst, said process comprising:

(a) combining a polyether polyol that contains zinc hexacyanocobaltate residues with aqueous isopropyl alcohol and an amount of EDTA effective to form an insoluble complex with the catalyst residues; and (b) filtering the resulting mixture to remove the insoluble complex from the polyol;

wherein the relative weight ratio of the polyether polyol to the aqueous isopropyl alcohol is within the range of about 2:1 to about 10:1, and wherein the aqueous isopropyl alcohol contains from about 50 to about 95 weight percent of isopropyl alcohol.

* * * * *